US007555101B2

(12) United States Patent
Maltz

(10) Patent No.: US 7,555,101 B2
(45) Date of Patent: Jun. 30, 2009

(54) HIGH-ENERGY PHOTON DETECTOR

(75) Inventor: Jonathan S. Maltz, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 185 days.

(21) Appl. No.: 11/510,482

(22) Filed: Aug. 23, 2006

(65) Prior Publication Data

US 2008/0049892 A1 Feb. 28, 2008

(51) Int. Cl.
*G01T 1/185* (2006.01)
(52) U.S. Cl. .......................... 378/98.8; 378/65; 250/389
(58) Field of Classification Search ................. 378/65, 378/98.8; 250/382, 389
See application file for complete search history.

(56) References Cited

U.S. PATENT DOCUMENTS

| 2,677,780 | A | * | 5/1954 | Rees et al. ..................... 313/93 |
| 3,230,372 | A | * | 1/1966 | Spracklen ................ 250/385.1 |
| 5,548,627 | A | * | 8/1996 | Swerdloff et al. ............. 378/65 |
| 7,030,386 | B2 | | 4/2006 | Pang et al. |
| 2003/0026386 | A1 | * | 2/2003 | Tang et al. ................... 378/154 |
| 2003/0169847 | A1 | * | 9/2003 | Karellas et al. ............ 378/98.3 |
| 2006/0050847 | A1 | * | 3/2006 | Jaffray et al. ................. 378/65 |

OTHER PUBLICATIONS

S.A. Watson et al., "Design, Fabrication and Testing of a Large anti-Scatter Grid for Megavolt X-Ray Imaging", 2005 IEEE Nuclear Science Symposium Conference Record, pp. 717-721, Oct. 2005.
Ralf Hinderer et al., "Development of a New Multielement Detector System for Megavoltage Photons", Cum Laude Poster, Proceedings of SPIE vol. 4682 (2002), pp. 809-818.
G. Pang and J. A. Rowlands, "Development of high quantum efficiency, flat panel, thick detectors for megavoltage x-ray imaging: A novel direct-conversion design and its feasibility", Medical Physics, vol. 31, No. 11, Nov. 2004, pp. 3004-3016.

* cited by examiner

*Primary Examiner*—Chih-Cheng G Kao

(57) ABSTRACT

A system may include a body defining a plurality of apertures, a plurality of conductive elements, each of the plurality of conductive elements disposed within a respective one of the plurality of apertures, an ionizable material disposed within each of the plurality of apertures, and a device coupled to each of plurality of conductive elements and to associate charge received from each of plurality of conductive elements with one or more respective image pixels.

19 Claims, 11 Drawing Sheets

HIGH-ENERGY PHOTON DETECTOR

BACKGROUND

1. Field

The embodiments described herein relate generally to systems for generating megavoltage radiation. More particularly, the described embodiments relate to imaging based on megavoltage radiation.

2. Description

A linear accelerator produces electrons or photons having particular energies. In one common application, a linear accelerator generates a radiation beam exhibiting megavoltage energies and directs the beam toward a target area of a patient. The beam is intended to destroy cells within the target area by causing ionizations within the cells or other radiation-induced cell damage.

Imaging systems may be used to verify patient positioning prior to the delivery of treatment radiation. According to some examples, a radiation beam is emitted by a linear accelerator prior to treatment, passes through a volume of the patient and is received by an imaging system. The imaging system produces a set of data that represents the attenuative properties of objects of the patient volume that lie between the radiation source and the imaging system.

The set of data is used to generate a two-dimensional portal image of the patient volume. The portal image will include areas of different intensities that reflect different compositions of the objects. For example, areas of low radiation intensity may represent bone and areas of high radiation intensity may represent tissue. Several two-dimensional portal images may be acquired from different perspectives with respect to the patient volume and combined to generate a three-dimensional image of the patient volume. The foregoing images may be used to diagnose illness, to plan radiation therapy, to confirm patient positioning prior to therapy, and/or to confirm a shape and intensity distribution of a radiation field prior to therapy.

Conventional imaging systems utilize thin (e.g., <1 mm) phosphor screens to convert incoming X-ray photons into light. The light is then converted into electric charge by an array of photodiodes. Such systems are efficient in converting low-energy X-rays (e.g. 0 to 250 keV) into light and therefore produce sufficiently detailed images when exposed to such X-rays. However, conventional thin screen-based systems are rather inefficient in stopping and converting megavoltage X-rays into light. As a result, conventional systems are unable to produce satisfactory images based on megavoltage radiation.

The above-mentioned stopping and converting efficiency may be improved by using thicker phosphor screens, but light spreading within such screens results in blurred images. Thick structured scintillator blocks composed of CsI needles have also been contemplated. Light transmission efficiency decreases as the thickness of such blocks increases, which leads to reduced total system sensitivity.

U.S. Pat. No. 7,030,386 describes a megavoltage radiation detector with improved quantum efficiency with respect to conventional systems. This detector is several centimeters thick and primarily composed of slabs exhibiting high electron density. Electrodes are placed within a lower density ionizable material (or a material capable of directly converting megavoltage radiation to electric charge) that is sandwiched between the slabs. In operation, an incident photon scatters in the slabs, electrons are produced by the scattering, the electrons ionize the ionizable material, and the resulting current flow is captured by an electrode located within the ionizable material. X-ray images are generated by recording these currents across a 2-D array of electrodes.

The foregoing detector presents several inefficiencies. These inefficiencies include a high manufacturing cost and poor scatter rejection. It would therefore be beneficial to provide a more suitable detector for generating satisfactory images based on incident megavoltage radiation. Such images may provide improved patient diagnosis, treatment planning and/or treatment delivery.

SUMMARY

In order to address the foregoing, some embodiments provide a body defining a plurality of apertures, a plurality of conductive elements, each of the plurality of conductive elements disposed within a respective one of the plurality of apertures, an ionizable material disposed within each of the plurality of apertures, and a device coupled to each of plurality of conductive elements and to associate charge received from each of plurality of conductive elements with one or more respective image pixels.

In some aspects, each of the plurality of apertures is substantially focused to a same point. Some aspects provide that the body is to receive megavoltage radiation following a divergent path, wherein an axis of each of the plurality of apertures is substantially aligned with the divergent path. Further to these aspects, a wall of each of the plurality of apertures may be substantially aligned with the divergent path.

Further aspects may include fabricating a body defining a plurality of apertures, placing one of a plurality of conductive elements within each of the plurality of apertures, filling each of the apertures with an ionizable material, and coupling a device to each of plurality of conductive elements, wherein the device is to associate charge received from each of plurality of conductive elements with one or more respective image pixels The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventor for carrying out some embodiments. Various modifications, however, will remain readily apparent to those in the art.

Figure 1:
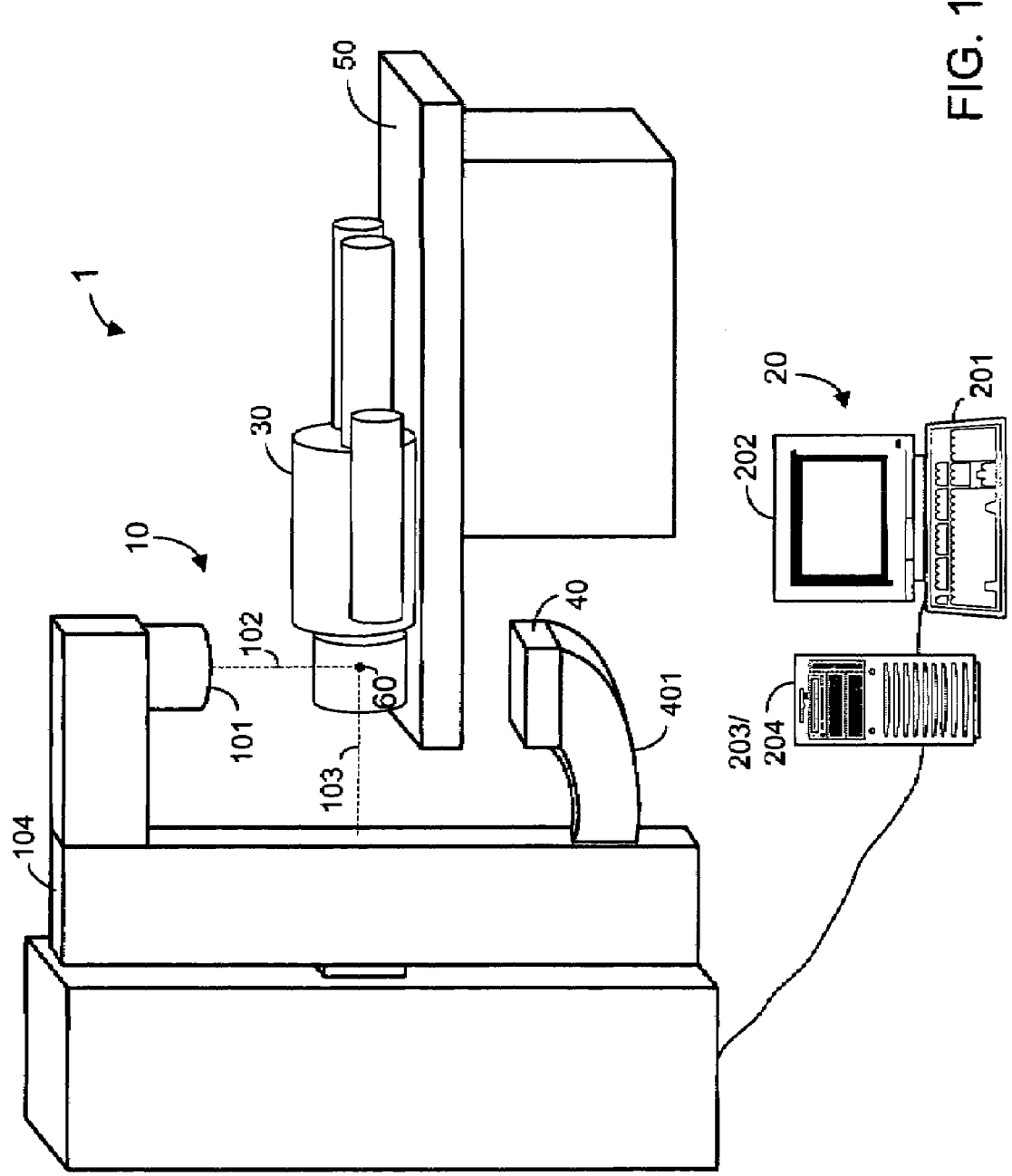
FIG. 1 is a perspective view of a linear accelerator system according to some embodiments.

FIG. 1 is a perspective view of system 1 according to some embodiments. Shown are linear accelerator 10, operator console 20, beam object 30, imaging device 40 and table 50. System 1 may be used to generate high-energy radiation for imaging and/or for medical radiation treatment. In this regard, beam object 30 may comprise a patient positioned to receive treatment radiation according to a radiation treatment plan. System 1 may be employed in other applications according to some embodiments.

Linear accelerator 10 generally delivers a high-energy (e.g., megavoltage) radiation beam from treatment head 101 toward a volume of object 30 at isocenter 60. Isocenter 60 may be located at an intersection of axis 102 of the aforementioned radiation beam and axis 103 around which gantry 104 is rotatable. According to some embodiments, the radiation beam may comprise photon or electron radiation. Although linear accelerator 10 is shown in FIG. 1, some embodiments are used in conjunction with Cobalt-60 or other radioisotope treatment machines.

Treatment head 101 includes a beam-emitting device (not shown) for emitting the radiation beam. Also included within treatment head 101 may be a beam-shielding device, or collimator, for shaping the beam and for shielding sensitive surfaces from the beam. Due to characteristic divergence of the radiation beam and the aforementioned shaping of the beam, the radiation beam delivers radiation to a radiation field rather than only to isocenter 60. An accessory tray may be mounted on treatment head 101 and configured to receive and securely hold attachments used during the course of treatment planning and treatment. These attachments may include an array of beam-attenuating elements, reticles, wedges, filters and/or apertures.

Imaging device 40 may acquire an image based on received photon radiation (i.e., X-rays) and/or electron radiation. The images may be acquired before, during and after radiation treatment. For example, imaging device 40 may acquire images for diagnosis, verification and recordation of a patient position, and verification and recordation of an internal patient portal to which treatment radiation is delivered. The effectiveness of radiation treatment often depends on the quality of these acquired images.

Imaging device 40 may be attached to gantry 104 in any manner, including via extendible and retractable housing 401. Rotation of gantry 104 may cause treatment head 101 and imaging device 40 to rotate around the isocenter such that isocenter 60 remains located between treatment head 101 and imaging device 40 during the rotation.

Table 50 supports object 30 during image acquisition and/or radiation therapy. Table 50 is adjustable to ensure, along with rotation of gantry 104, that a volume of interest is positioned between treatment head 101 and imaging device 40. Table 50 may also be used to support devices used for acquisition of correction images, other calibration tasks and/or beam verification.

Operator console 20 includes input device 201 for receiving instructions from an operator such as an instruction to acquire an image based on emitted megavoltage radiation and an instruction to deliver treatment radiation according to a treatment plan. Console 20 also includes output device 202, which may be a monitor for presenting operational parameters of linear accelerator 10 and/or interfaces for controlling systems 10, 40 and/or 50. Output device 202 may also present images acquired by imaging device 40. Input device 201 and output device 204 are coupled to processor 203 and storage 204.

Processor 203 executes program code according to some embodiments. The program code may be executable to control system 1 to operate as described herein. The program code may be stored in storage 204, which may comprise one or more storage media of identical or different types, including but not limited to a fixed disk, a floppy disk, a CD-ROM, a DVD-ROM, a Zip™ disk, a magnetic tape, and a signal. Storage 204 may, for example, store radiation treatment plans, portal images, software applications to calibrate system 1 and/or to provide radiation treatment, and other data used to perform radiation treatment.

Operator console 20 may be located apart from linear accelerator 10, such as in a different room, in order to protect its operator from radiation. For example, accelerator 10 may be located in a heavily shielded room, such as a concrete vault, which shields the operator from radiation generated by accelerator 10.

Each of the devices shown in FIG. 1 may include less or more components than those shown. In addition, embodiments are not limited to the components shown in FIG. 1.

Figure 2:
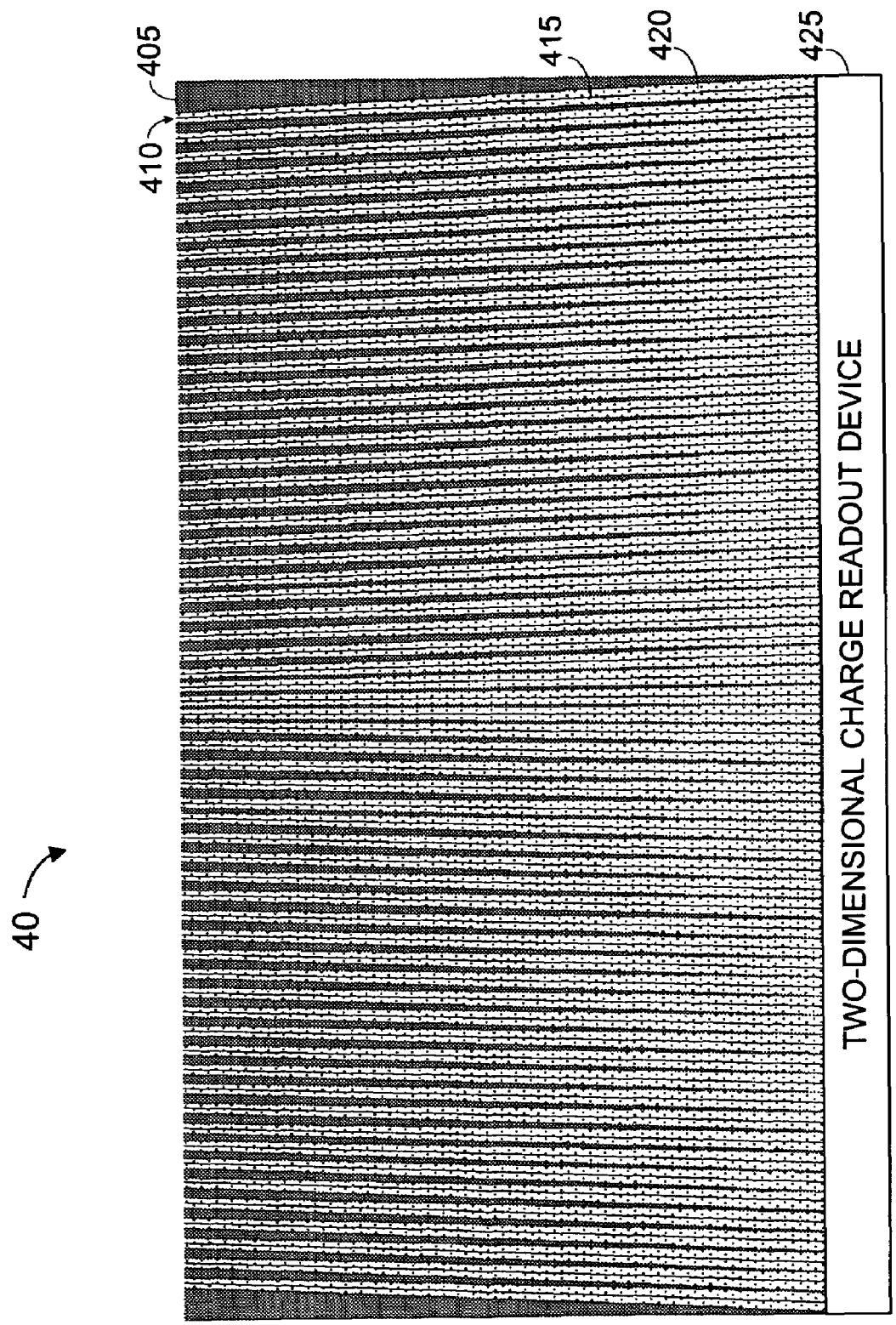
FIG. 2 is a cross-sectional view of an apparatus according to some embodiments.

FIG. 2 is a cross-sectional view of imaging device 40 according to some embodiments. Imaging device 40 comprises body 405 defining a plurality of apertures 410. A conductive element 415 and an ionizable material 420 are disposed in each aperture 410. Each of conductive elements 415 is coupled to device 425. Device 425 is to associate charge received from each of conductive elements 415 with one or more respective image pixels. Further operational details will be set forth below.

Figure 3:
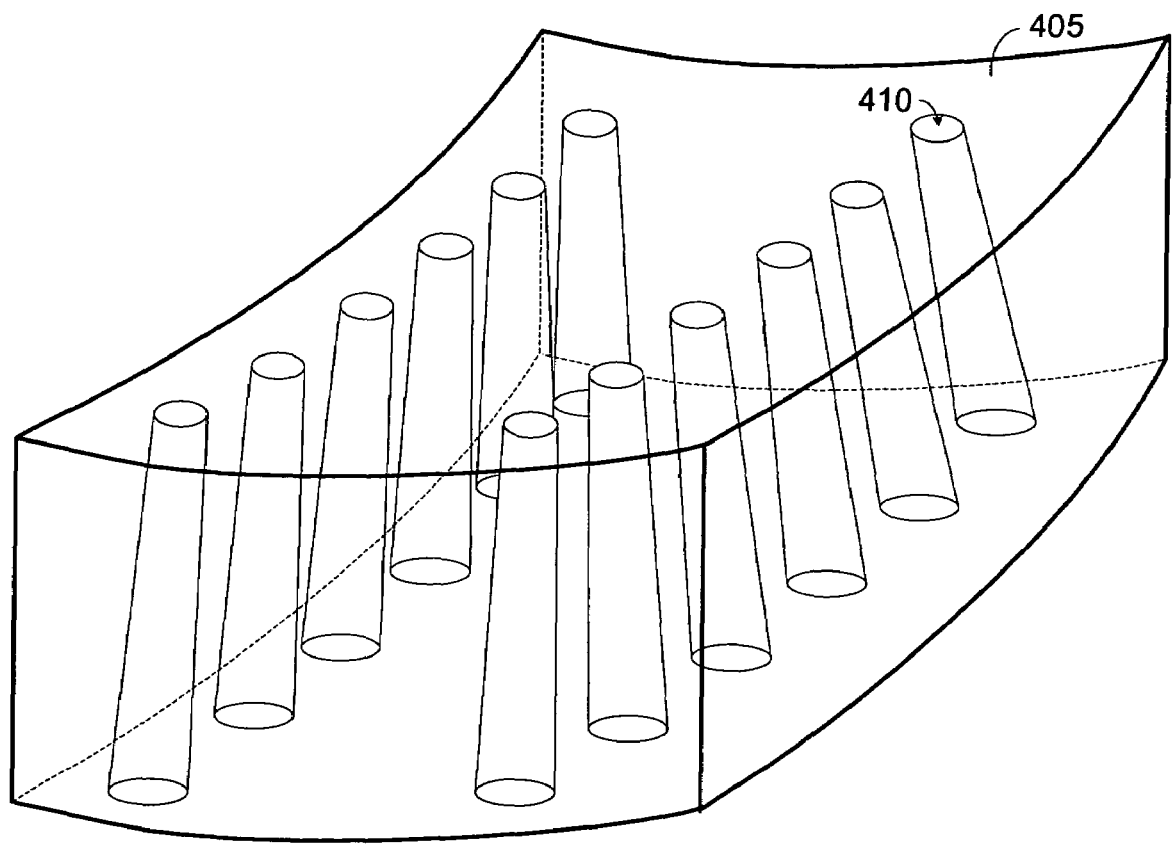
FIG. 3 is a transparent perspective view of a body of an apparatus according to some embodiments.

FIG. 3 is a transparent perspective view of a portion of body 405 for further illustrating the construction thereof. Conductive elements 415 and ionizable material 420 have been omitted from FIG. 3 for clarity. According to the illustrated embodiment, each of apertures 410 is substantially focused to a same point.

Body 405 may comprise a Potter-Bucky grid comprising one or more materials exhibiting a high electron density. According to some embodiments, body 405 comprises a tungsten powder and epoxy mixture exhibiting a density of 11.8 g/cm$^3$. An actual implementation of body 405 may define thousands of apertures, with each aperture to provide a measurement corresponding to a single image pixel.

Figure 4:
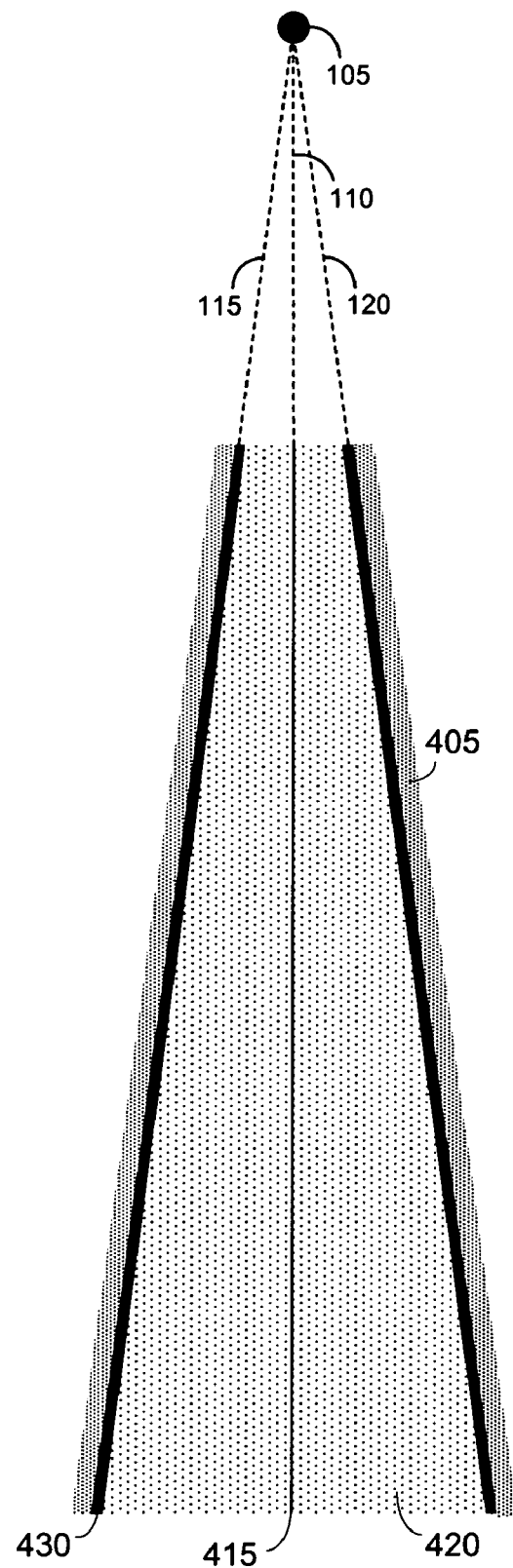
FIG. 4 comprises a cross-sectional side view of an aperture of an apparatus according to some embodiments.

FIG. 4 comprises a cross-sectional view of an aperture 410 according to some embodiments. As shown, body 405 defines outer walls of aperture 410 and conductor 430 is disposed on the walls. Ionizable material 420 is disposed between conductive element 415 and conductor 430.

Ionizable material 420 may comprise any material(s), including gases, that may receive scatter radiation from body 405 and produce electron-hole pairs in response thereto. Ionizable material 420 may also or alternatively comprise a material or materials capable of directly converting received megavoltage photons into electric charge (e.g., mercury-iodine or amorphous selenium). An electrical insulator may be placed on conductor 430 if a conductivity of ionizable material 420 is such that charge may flow between conductor 430 and conductive element 415 in the absence of ionization.

FIG. 4 also illustrates a physical relationship between aperture 410 and radiation source 105 according to some embodiments. As shown, radiation emitted from radiation source 105 follows a divergent path delineated by dotted lines 115 and 120. The walls of aperture 410 defined by body 405 are substantially aligned with the divergent path according to some embodiments. An axis of aperture 410 is also substantially aligned with the divergent path (i.e., with axis 110 of the divergent path). Each aperture 410 of body 405 may be substantially focused to a same spot of megavoltage radiation source according to some embodiments.

Figure 5A:
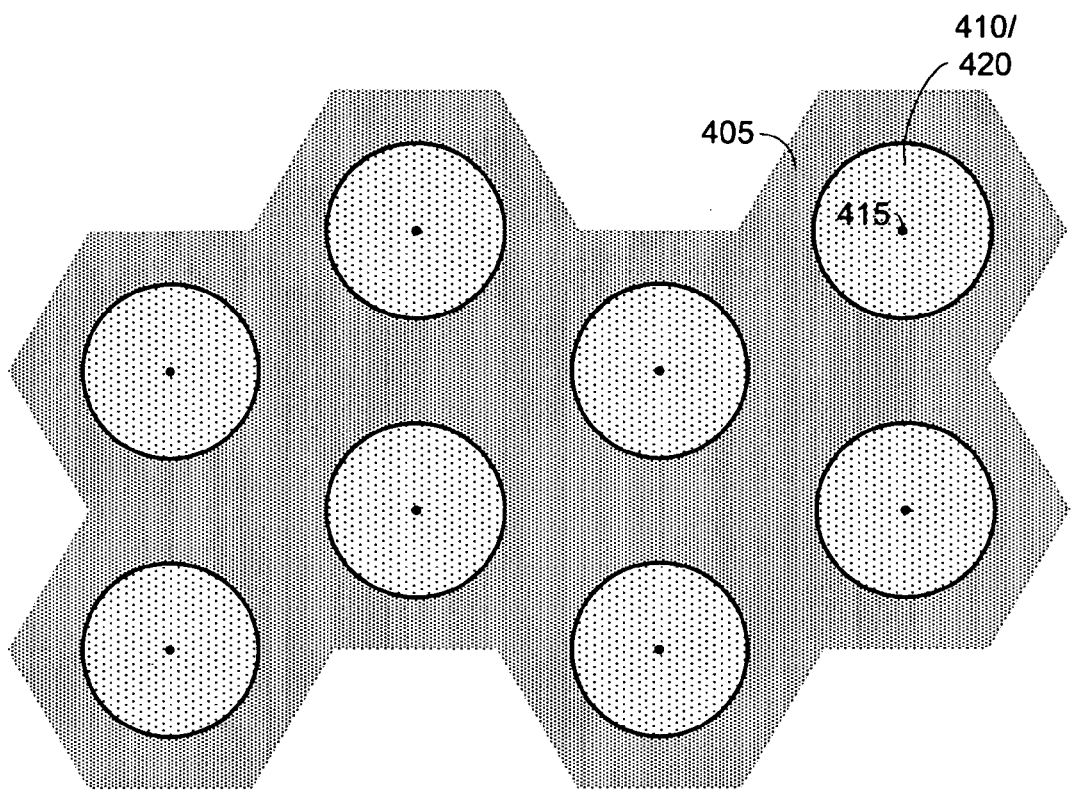
FIGS. 5A and 5B comprise top and bottom perspective views of portions of an apparatus according to some embodiments.
Figure 5B:
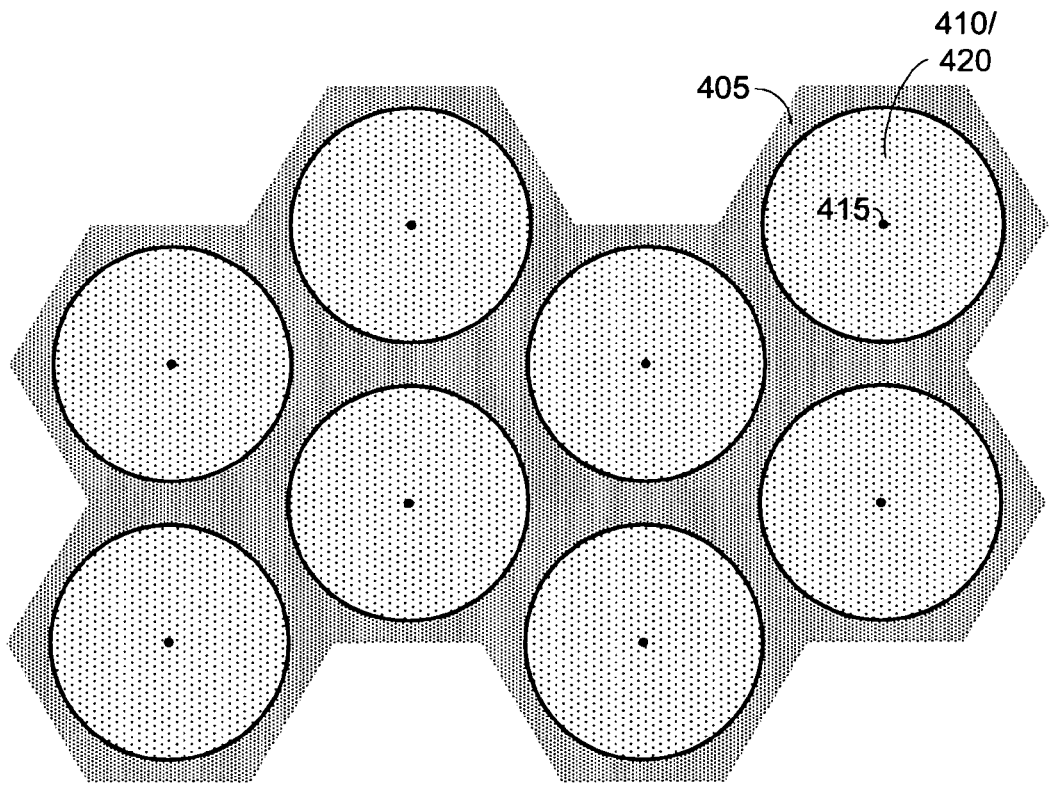

FIGS. 5A and 5B comprise top and bottom views, respectively, of body 405 to provide even further illustration of the construction of device 40 according to some embodiments. The diameter of apertures 410 is larger at the bottom of body 405 than at the top of body 405 due to the previously-described shape thereof.

In operation, a positive potential is applied to conductor 430 with respect to ground of linear accelerator 10. Megavoltage radiation is emitted from treatment head 101 while a volume of interest is located between treatment head and imaging device 40. Body 405 receives radiation attenuated by the volume and high-energy electrons are generated as a result. As mentioned above, body 405 receives radiation from a Cobalt-60 or other radioisotope treatment machine in some embodiments.

The high-energy electrons enter an aperture 410 and cause ionizable material 420 located therein to generate electrical charge. In a case that ionizable material 420 is a "direct conversion" material, the electrical charge is generated in response to reception of direct (non-scatter) radiation received from treatment head 110. In either case, the generated charge is collected by a conductive element 415 within the aperture 410 and transmitted to charge readout device 425. In some embodiments, the charge is associated with an image pixel and used to determine a value of the image pixel. By receiving charge from each conductive element 415 of body 405, device 425 may determine values of each image pixel in a portal image.

Figure 6:
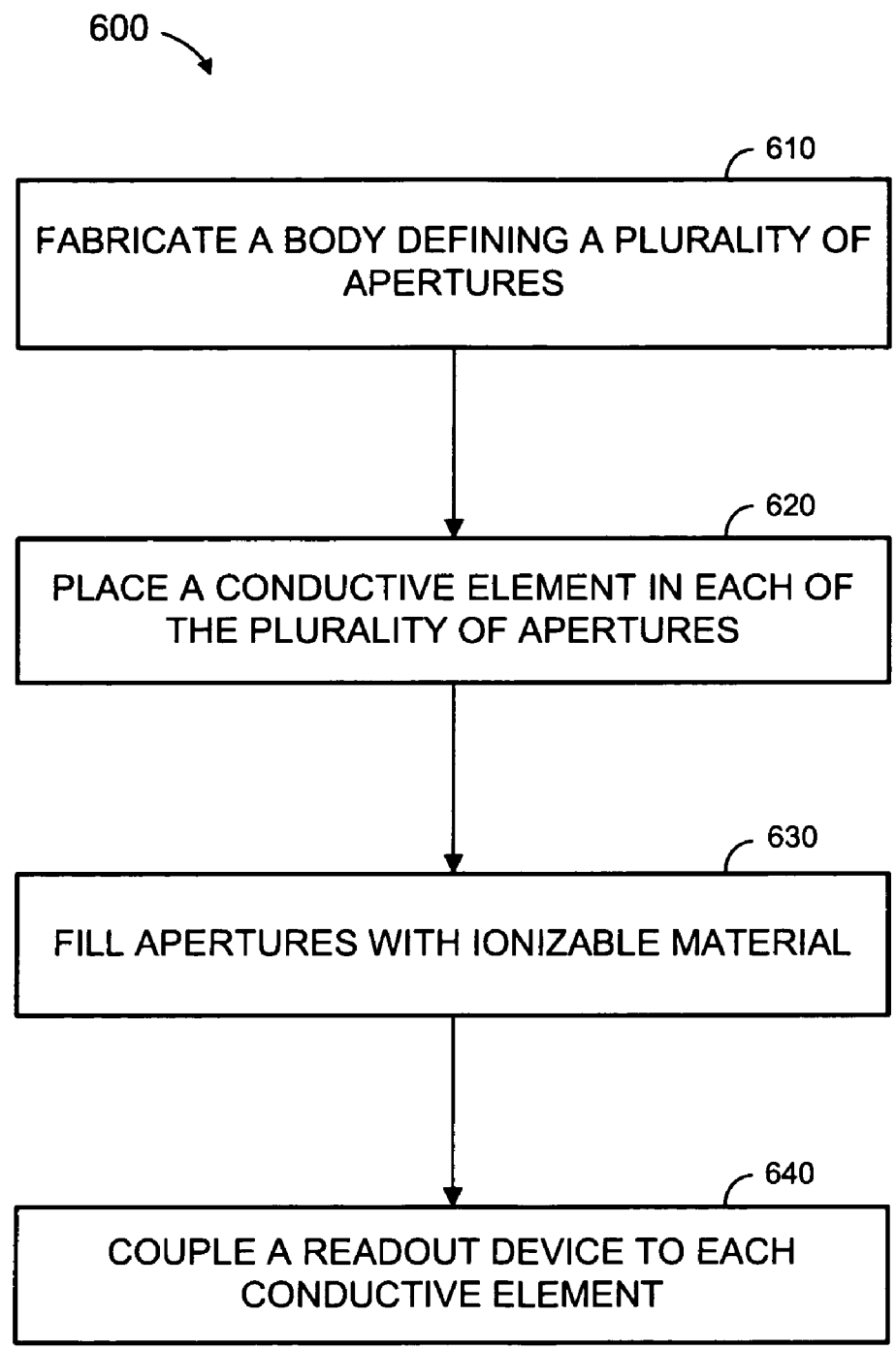
FIG. 6 comprises a flow diagram according to some embodiments.

FIG. 6 if a flow diagram of process 600 to fabricate an apparatus according to some embodiments. Process 600 may be performed by one or more entities, and significant periods of time may elapse between each element of process 600.

Initially, a body defining a plurality of apertures is fabricated at 610. According to some embodiments, tungsten powder and epoxy are placed in an aluminum mold at 610. Suitable and known techniques for hardening the mixture and removing the hardened body from the mold are then employed.

Figure 7:
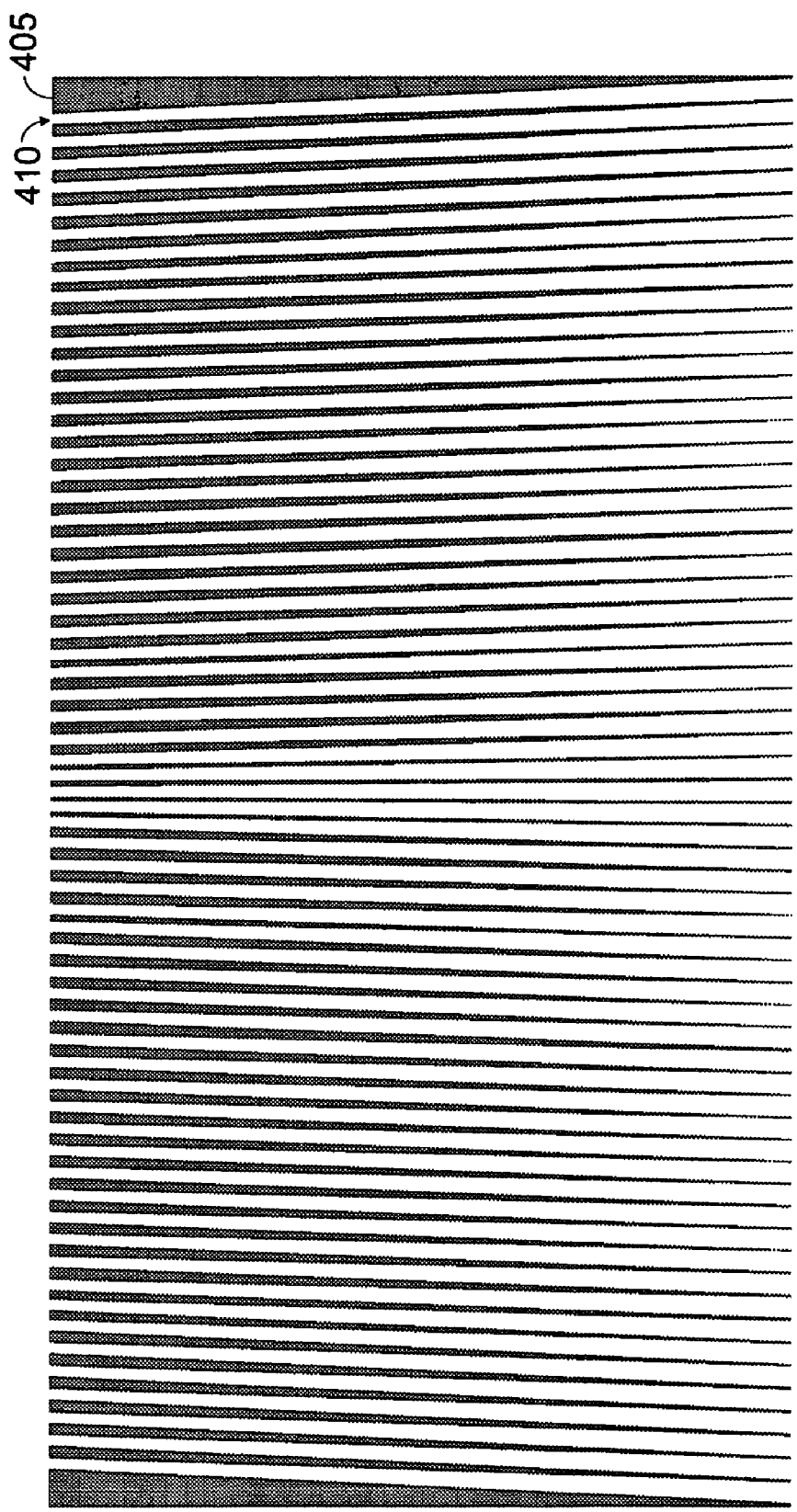
FIG. 7 is a cross-sectional view of an apparatus during fabrication according to some embodiments.

FIG. 7 is a cross-sectional view of body 405 after some embodiments of 610. As shown, body 405 defines a plurality of apertures 410. As described above, the apertures 410 are substantially focused to a same point. A wall of each of the plurality of apertures may be aligned with a divergent path along which body 405 is to receive megavoltage radiation.

The inside of each aperture (or, the entire body) may be coated with a conductive material (e.g., copper or gold) after 610. An electrical insulator may then be deposited on the conductive material if deemed necessary. As mentioned above, the electrical insulator may be required to prevent undesirable charge flow between the conductive material within an aperture and a conductive element placed in each aperture.

Figure 8:
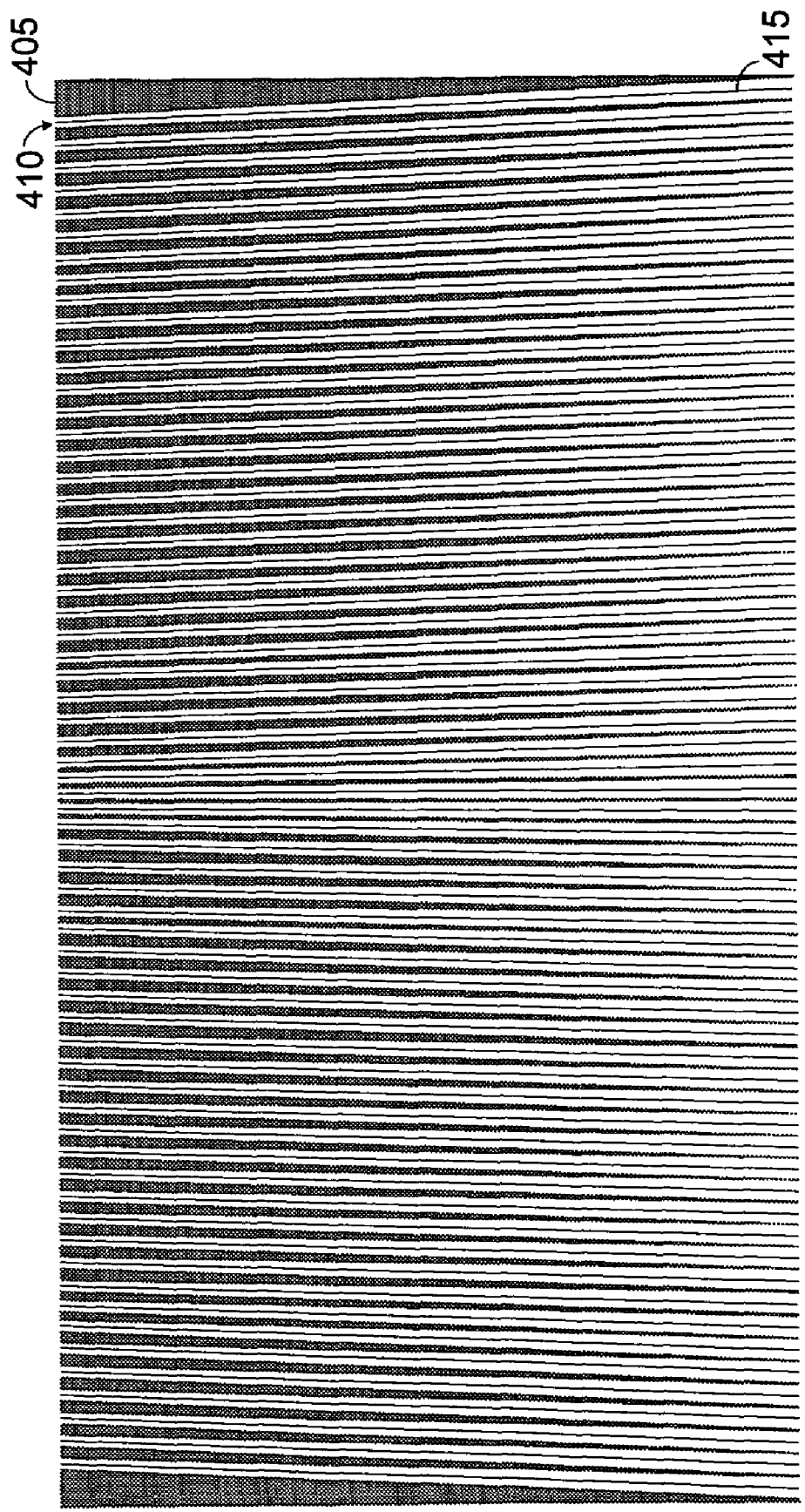
FIG. 8 is a cross-sectional view of an apparatus during fabrication according to some embodiments.

In this regard, a conductive element is placed in each aperture at 620. FIG. 8 is a cross-sectional view of body 405 after placement of a conductive element 415 within each aperture 410. The remaining volume of each aperture 410 is filled with ionizable material at 630. Again, the ionizable material may be ionizable in response to high-energy electrons produced in scattering events or in response to megavoltage photons. Body 405 may be sealed from the atmosphere and pressurized in a case that the ionizable material is a gas (e.g., xenon).

Figure 9B:
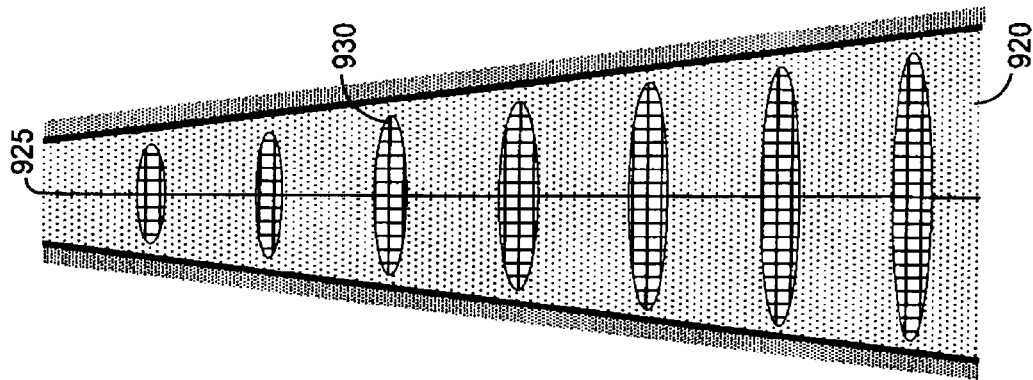
FIGS. 9A and 9B comprise cross-sectional side views of an aperture of an apparatus according to some embodiments.
Figure 9A:
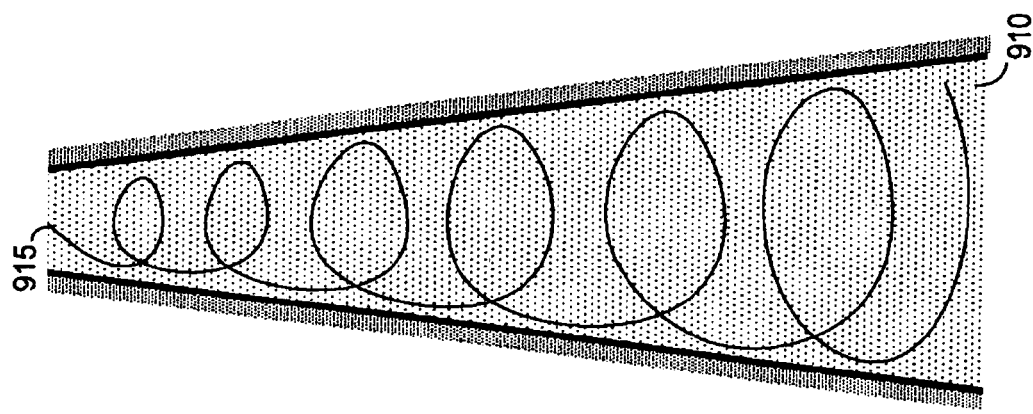

FIGS. 9A and 9B are cross-sectional views of apertures of an apparatus according to some embodiments. Apertures 910 and 920 are identical to aperture 410 of FIG. 4 but for different geometries of the conductive elements disposed therein. Specifically, conductive element 915 comprises a helical-shaped element and conductive element 925 comprises a plurality of conductive disks 930.

Both of conductive elements 915 and 925 are in contact with more ionizable material than conductive element 415. Each of conductive disks 930, for example, exhibits a diameter that is based on a diameter of aperture 920 at a location of the conductive disk 930. Conductive elements 915 and 925 may provide increased charge collection efficiency and speed in comparison to conductive element 415. In some embodiments, the conductive element within an aperture comprises a conductive mesh that fills the aperture. Accordingly, the inner walls of the aperture may be coated with an insulator to avoid shorting the conductive element against the conductor disposed on the walls.

A readout device is coupled to each conductive element at 640. The readout device may comprise a charge amplifier to integrate electrical charge received from the conductive elements. The charge may be integrated with respect to linear accelerator ground. The integrated charge may be used to determine pixel values of a two-dimensional image. In some embodiments, charge received from a single conductive element 415 is used to determine a value of an image pixel associated with the single conductive element. A value of a single image pixel may be determined based on charge received from several conductive elements 415, and, conversely, values of several image pixels may be determined based on charge received from a single conductive elements 415. FIG. 2 illustrates an apparatus fabricated according to some embodiments of process 600.

Figure 10:
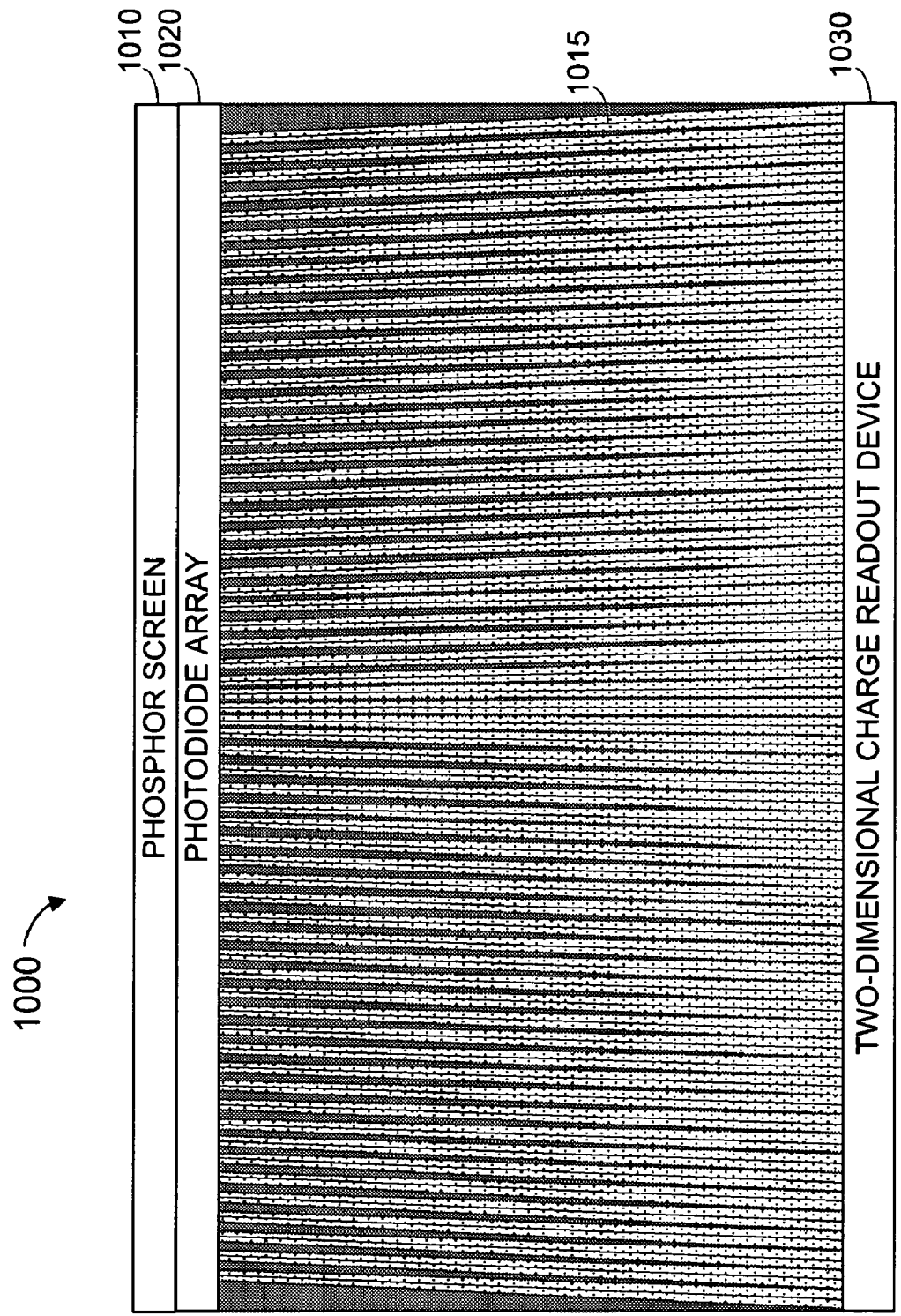
FIG. 10 comprises an apparatus to generate an image based on kilovoltage radiation and megavoltage radiation according to some embodiments.

FIG. 10 is a cross-sectional view of apparatus 1000 according to some embodiments. Apparatus 1000 may comprise any embodiment of a body, apertures, conductive elements and ionizable material described herein or known in the art. Apparatus 1000 also includes phosphor screen 1010 and photodiode array 1020 for detecting low-energy (e.g. kilovoltage) radiation.

Phosphor screen 1010 receives low-energy photon radiation that is emitted by treatment head 110 along with megavoltage radiation. Phosphor screen 1010 generates light in proportion to the intensity of the received low-energy radiation. Photodiode array 1020 receives the light and records the intensity of received light as stored electrical charge. The stored charge may be read out and used to augment image pixel values produced by readout device 1030, which may operate as described above based on megavoltage radiation that simply passes through screen 1010 and array 1020. In some embodiments, each conductive element 1015 and photodiode is associated with a single image pixel, and the charge collected/stored thereby is used to determine a value of the single image pixel.

Figure 11:
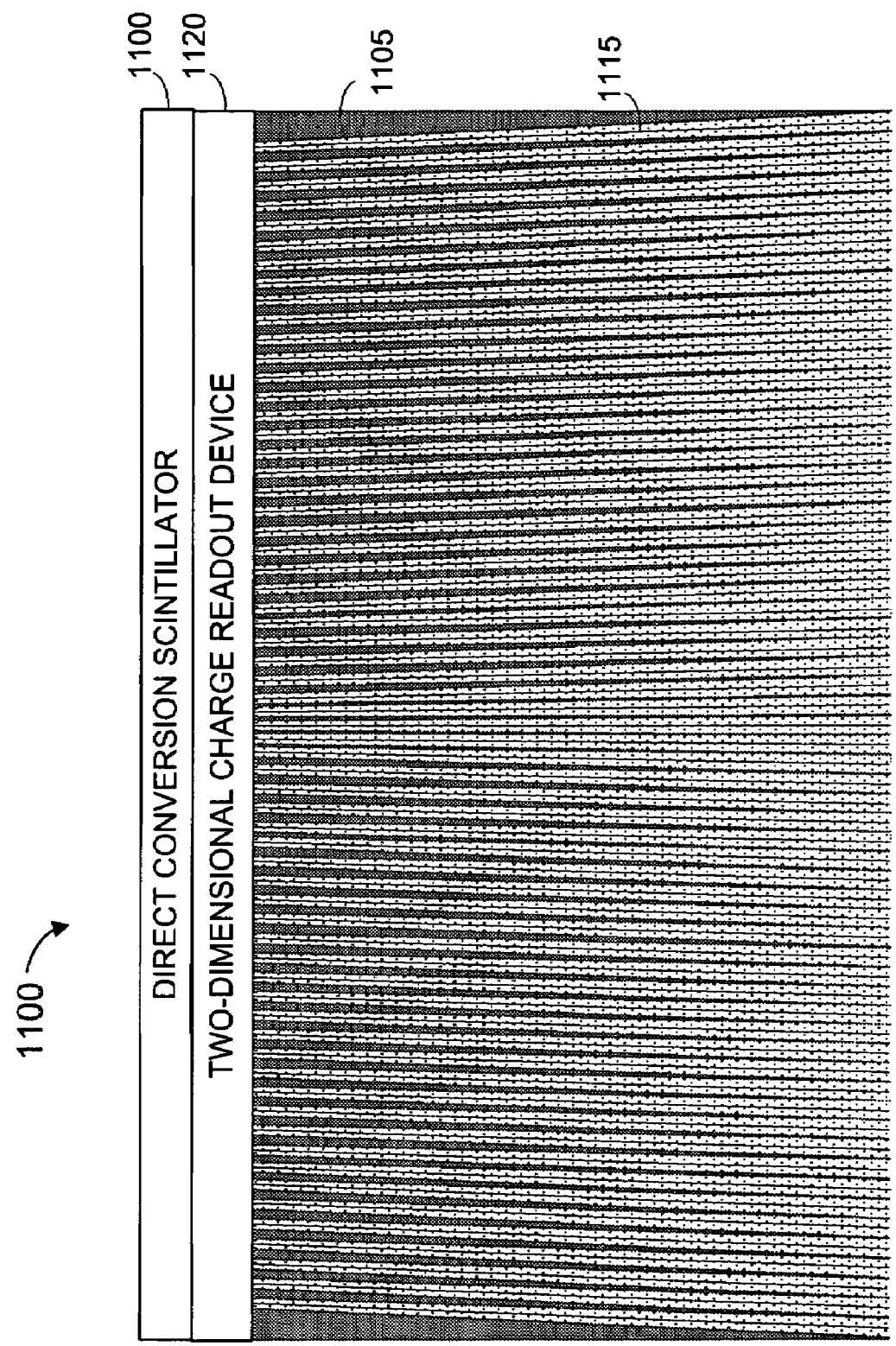
FIG. 11 comprises an apparatus to generate an image based on kilovoltage radiation and megavoltage radiation according to some embodiments.

FIG. 11 is a cross-sectional view of apparatus 1100 according to some embodiments. Apparatus 1100 may also comprise any embodiment of a body, apertures, conductive elements and ionizable material described herein or known in the art. However, apparatus 1100 also includes direct conversion scintillator 1110 coupled to readout device 1120.

In operation, scintillator 1110 converts received low-energy photons to electrical charge which is collected by readout device 1120. Readout device 1120 also collects electrical charge from conductive elements 1115 due to megavoltage radiation received by body 1105. According to some embodiments, a conductive element 1115 corresponding to an image pixel is connected to a circuit of device 1120 that also collects electrical charge corresponding to the image pixel from scintillator 1110.

According to some embodiments, the apertures discussed above may be slightly defocused from an anticipated radiation source location. Such an arrangement may increase interaction between photons received directly from the radiation source and regions of the aforementioned body that are located adjacent to the apertures. The increased interaction may result in increased ionizations within the apertures. Alternatively, the body may be fabricated from multiple horizontal slabs having focuses shifted relative to each other. During irradiation, this arrangement may result in electron build-up regions between the slabs and increased ionizations.

The several embodiments described herein are solely for the purpose of illustration. Therefore, persons in the art will recognize from this description that other embodiments may be practiced with various modifications and alterations.

What is claimed is:

1. An apparatus comprising:
   a body defining a plurality of apertures, wherein each of the plurality of apertures defines a first opening and a second opening, wherein each of the plurality of apertures is conically-shaped, and wherein the first opening is smaller than the second opening;
   a plurality of conductive elements, each of the plurality of conductive elements disposed within a respective one of the plurality of apertures;
   an ionizable material disposed within each of the plurality of apertures; and
   a device coupled to each of the plurality of conductive elements and to associate charge received from each of the plurality of conductive elements with one or more respective image pixels.

2. An apparatus according to claim 1, wherein the ionizable material is to receive megavoltage radiation and to generate charge in response thereto.

3. An apparatus according to claim 1, wherein each of the plurality of apertures is substantially focused to a same point.

4. An apparatus according to claim 1, wherein the body is to receive megavoltage radiation,
   wherein the radiation follows a divergent path, and
   wherein an axis of each of the plurality of apertures is substantially aligned with the divergent path.

5. An apparatus according to claim 4, wherein a wall of each of the plurality of apertures is substantially aligned with the divergent path, and wherein a conductor is disposed on each wall of the plurality of apertures.

6. An apparatus according to claim 1, wherein each of the plurality of conductive elements comprises a wire aligned along an axis of one of the plurality of apertures and a plurality of conductive disks coupled to the wire,
   wherein a diameter of a conductive disk is based on a diameter of an aperture at a location of the conductive disk.

7. An apparatus according to claim 1, wherein each of the plurality of conductive elements comprises a helical-shaped element.

8. An apparatus according to claim 1, further comprising:
   a second device to receive kilovoltage radiation and to generate visible light in response thereto; and
   a third device to receive the visible light, to generate second charge in response thereto, and to associate the second charge with the one or more respective image pixels.

9. An apparatus according to claim 1, further comprising:
   a second device coupled to the device, the second device to receive kilovoltage radiation and to generate second charge in response thereto,
   wherein the device is to associate the second charge received from the second device with the one or more respective image pixels.

10. A method comprising:
    fabricating a body defining a plurality of apertures, wherein each of the plurality of apertures defines a first opening and a second opening, wherein each of the plurality of apertures is conically-shaped, and wherein the first opening is smaller than the second opening;
    placing one of a plurality of conductive elements within each of the plurality of apertures;
    filling each, of the apertures with an ionizable material; and
    coupling a device to each of the plurality of conductive elements,
    wherein the device is to associate charge received from each of the plurality of conductive elements with one or more respective image pixels.

11. A method according to claim 10, wherein the ionizable material is to receive megavoltage radiation and to generate charge in response thereto.

12. A method according to claim 10, wherein each of the plurality of apertures is substantially focused to a same point.

13. A method according to claim 10, wherein the body is to receive megavoltage radiation,
    wherein the radiation follows a divergent path, and
    wherein an axis of each of the plurality of apertures is substantially aligned with the divergent path.

14. A method according to claim 13, wherein a wall of each of the plurality of apertures is substantially aligned with the divergent path, and wherein a conductor is disposed on each wall of the plurality of apertures.

15. A method according to claim 10, wherein each of the plurality of conductive elements comprises a wire aligned along an axis of one of the plurality of apertures and a plurality of conductive disks coupled to the wire,
    wherein a diameter of a conductive disk is based on a diameter of an aperture at a location of the conductive disk.

16. A method according to claim 10, wherein each of the plurality of conductive elements comprises a helical-shaped element.

17. A method according to claim 10, further comprising:
    coupling a second device and a third device to the body,
    wherein the second device is to receive kilovoltage radiation and to generate visible light in response thereto, and
    wherein the third device is to receive the visible light, to generate second charge in response thereto, and to associate the second charge with the one or more respective image pixels.

18. A method according to claim 10, further comprising:
    coupling a second device to the device,
    wherein the second device is to receive kilovoltage radiation and to generate second charge in response thereto, and wherein the device is to associate the second charge received from the second device with the one or more respective image pixels.

19. A method according to claim 10, further comprising:

emitting megavoltage radiation toward the body from a megavoltage radiation source;

receiving the charge from each of the plurality of conductive elements using the device; and associating the received charge with the one or more respective image pixels using the device.

* * * * *